(12) United States Patent
Maurer-Spurej

(10) Patent No.: US 7,341,873 B2
(45) Date of Patent: Mar. 11, 2008

(54) METHOD FOR DETERMINATION OF PLATELETS QUALITY

(75) Inventor: Elisabeth Maurer-Spurej, Vancouver (CA)

(73) Assignee: Canadian Blood Services, Ontario (CA)

( * ) Notice: Subject to any disclaimer, the term of this patent is extended or adjusted under 35 U.S.C. 154(b) by 464 days.

(21) Appl. No.: 10/925,779

(22) Filed: Aug. 24, 2004

(65) Prior Publication Data

US 2006/0046280 A1 Mar. 2, 2006

(51) Int. Cl.
G01N 33/48 (2006.01)
A61K 35/12 (2006.01)
A61K 35/14 (2006.01)

(52) U.S. Cl. ............... 436/63; 435/325; 435/287.1; 435/808; 424/532

(58) Field of Classification Search ............... None
See application file for complete search history.

(56) References Cited

U.S. PATENT DOCUMENTS 4,080,264 A 3/1978 Cohen et al.
5,817,519 A 10/1998 Zelmanovic et al.

FOREIGN PATENT DOCUMENTS

WO WO-90/14588 11/1990

OTHER PUBLICATIONS

Abrams, C.S., et al., Blood. 1990. 75(1), 128-138.*
Cram, S.L. Methods in Cell Science. 2002, 24(1-3), 1-9.*
Hoffmeister, K.M., et al. Cell. 2003.112(1), 87-97.*
Rock, G. et al. Transfusion and Apheresis Science. 2006. 35, 145-149.*
Fratantoni et al., *J. Lab. Clin. Med.*, vol. 103 (4), pp. 620-631 (1984).
David et al., *Coll. Surfaces B.: Biointerfaces*, vol. 6 pp. 101-114 (1996).
Hubbell et al., *Thromb Haemost*, vol. 65, pp. 601-607, (1991).
Maurer-Spurej et al., *Lab. Invest.*, vol. 81 (4), pp. 581-592 (2001).
Spurej et al., *Experientia*, vol. 48, pp. 71-79 (1992).
D. Zelmanovic et al., *Vet. Clin. Pathol.*, vol. 27 (1), pp. 2-9 (1998).
Eto et al., *Cardiovascular Research*, vol. 40 (1), pp. 223-229 (1998).
Tomida et al., *Thromb. Res.*, vol. 92, pp. 221-228 (1998).
Yabusaki et al., *Langmuir*, vol. 18, pp. 39-45 (2002).
J. Seghatchian et al., "Transfus. Sci.", vol. 18, No. 1, pp. 27-32 (1997).
Database Biosis, XP-002361280 (2002).
Devine, D. V., et al., "Platelet Aggregation is Not Initiated by Platelet Shape Change", Laboratory Investigation, Nov. 2001, vol. 81, pp. 1517-1525.
Devine D. V., et al., "Room Temperature Activiates Human Blood Platelets", Laboratory Investigation, Apr. 2001, vol. 81, No. 4, pp. 581-592.
Maurer-Spurej, E. et al., "Activation Studies on Human Platelets Using Electrophoretic and quasi-elastic light scattering", Progress in Colloid & Polymer Science, 1990, -vol. 81: 151-155.
Pfeifer G., et al., Shape Change of Human Blood Platelets: Reliable and Fast Detection by Quasi-Elastic Light Scattering, 1991, Institute for Physikahsche Chemic.
Devine V. D., et al., 504 "Temperature Induced Shape Change of Human Blood Platelets and Its Possible Physiological Relevance", University of British Columbia, Department of Pathology, Vancouver, BC, Canada, date unknown.
Devine D. V., et al., SP254, "Platelet Shape Change is Not Required for Aggregation-Initail Decrease of Light Transmmision in Platelet Aggregometry Indicates Platelet Micro-Aggregation But Not Shape Change", Transfussion, 2000—vol. 40, Supplement.
Maurer-Spurej, E., SP145, "Novel Dynamic Light Sctattering Method for the Dertermination of Platelet Quality and Viability", Canadian Blood Services, Canada, Transfusion, 2004—vol. 44, Supplement.

* cited by examiner

*Primary Examiner*—Sandra E. Saucier
*Assistant Examiner*—Aaron J. Kosar
(74) *Attorney, Agent, or Firm*—Christine C. O'Day; Matthew Beaudet; Edwards Angell Palmer & Dodge LLP

(57) ABSTRACT

There is provided a method for assessing the quality of platelet concentrates for determining their suitability for transfusion. More specifically dynamic light scattering measurements of the samples containing platelets are obtained and parameters, such as hydrodynamic radius and relative number of platelet-derived microparticles, are derived from these measurements that are indicative of platelet quality.

15 Claims, 5 Drawing Sheets

DIC micrographs

METHOD FOR DETERMINATION OF PLATELETS QUALITY

CROSS-REFERENCE TO RELATED APPLICATIONS

This is the first application filed for the present invention.

TECHNICAL FIELD

This application relates to measurement of platelet quality and more particularly the measurement of platelet quality using light scattering.

BACKGROUND OF THE INVENTION

Poor quality of platelet concentrates obtained from donors correlates with low efficiency and increased risk for adverse reactions in recipients. The circulation half-life of platelets is about 5 days after which time they become senescent i.e. undergo a number of physiological changes that leads to their ultimate removal from the circulation primarily by macrophages in the spleen and liver. In order to keep platelets in concentrates (i.e., under highly artificial conditions) alive for at least 5 days, platelet activation has to be inhibited. Calcium chelators and the pH lowering effect of anticoagulants (Bouchard et al. Interactions between platelets and the coagulation system. In: Platelets. Ed: Michelson A D.), gentle preparation techniques (Hagberg et al. *Transfusion.* 2000; 40(2):182-192.) and the use of biocompatible materials for tubing and containers (Iwasaki et al. *J Biomed Mater Res.* 2001; 57(1):72-8.) contribute to preserving platelet integrity; however, during storage platelets lose their integrity and viability, a phenomenon generally known as the platelet storage lesion (Devine et al. *Transfusion.* 1999; 39(7):724-734.) Some characteristics of activated fresh platelets can be found in old stored platelets such as increased P-selectin expression (Barnard et al. *Transfusion.* 1999; 39(8; 850-8.) and increased number of microparticles. Microparticles are either budded from the plasma membrane or released during secretion and range in size between 40 nm and 1 μm (Nieuwland R, Sturk A. Platelet-derived microparticles. In: Platelets. (editor: A D Michelson). Academic Press 2002; 255-65.). Other indicators such as responsiveness to physiologic agonists are modified in stored platelets (Curvers et al. *Transfusion.* 2004; 44(1):49-58.).

At present the determination of platelet quality is very laborious and time consuming because no single test exists for this purpose. Thus, a whole panel of parameters is usually investigated. These include platelet morphology scoring (Rock et al. *Transfusion.* 2003; 43(10):1374-7.), the expression of activation markers on the platelet surface (Holme et al. *Transfusion.* 1997; 37(1):12-17.) and the presence and characterization of platelet microparticles with flow cytometry (Kim et al. *Blood Coagul Fibrinolysis.* 2002; 13(5):393-397.), the response to hypotonic shock (Holme et al. *Transfusion.* 1998; 38(1):31-40.), the extent of shape change (Hunter et al. *Transfusion.* 2001; 41(6):809-14; Holme et al. *Transfusion.* 1997; 37(1):5-11.) and, more recently, the detection of platelet mitochondrial activity (Pich et al. *Free Radic Res.* 2002; 36(4):429-436; Perrotta et al. *Transfusion.* 2003; 43(4):526-35.). Manual morphology scoring on the microscope is an integral part of platelet characterization in transfusion medicine and has been proven to be one of the best in vitro tests for platelet quality (Kunicki et al. *Transfusion.* 1975; 15(5): 414-421.) with good correlation to in vivo survival time (Slichter S J, Harker L A. *Br J Haematol.* 1976; 34(3):395-402; Slichter S J, Harker L A. *Br J Haematol.* 1976; 34(3):403-19.). However, morphology scoring on the microscope is time consuming and subjective and accordingly is not practical for rapidly testing large batches of platelet concentrates.

Optical methods have been proposed and developed to measure platelet quality but they suffer shortcomings that prevent their use in routine quality determination. For example, the so-called swirling effect is a simple but crude and subjective test for the discoid shape of platelets in concentrates. Platelet monitoring using the swirling effect routinely in an automated device (Bellhouse et al. *Br J Haematol.* 1987; 66(4):503-8.) has not proven successful.

Light transmission measured in an aggregometer reflects the responsiveness of platelets to exogenous agonists (Bom G V R, Thorngren M. *Brit J Radiol.* 1985; 58 (693):922-923; Born G V R. Adv Exp Med Biol 1985; 192: 399-409.). While this test is easy to perform, it requires large sample volumes (0.5 mL) and a control sample for each run. Although the initial decrease in light transmission after addition of an agonist has been previously reported to reflect platelet shape change by Latimer at al. (Latimer et al. *Arch Biochem Biophys.* 1977; 180:151-159.), it has later been questioned (Latimer P. *Appl Opt.* 1983; 22:1136-1143.). It has now been shown that this signal is caused by platelet microaggregation (Maurer-Spurej E, and Devine D V. *Lab Invest.* 2001; 81(11): 1517-26.). If platelets are preactivated, for example by exposure to room temperature, the kinetics of aggregation are enhanced and light transmission decreases immediately (Maurer-Spurej E, and Devine D V. *Lab Invest.* 2001; 81(11): 1517-26.). The instrument developed by ChronoLog that utilizes the initial decrease in light transmission as an indicator of platelet quality, therefore, measures the extent of microaggregation rather than the "extent of shape change".

Static light scattering measures the intensity of the scattered light at different scattering angles which results in an average particle size and optical density (Fratantoni et al. *Lab Clin Med.* 1984; 103(4):620-31.). Platelet shape change has only a minor effect on the actual platelet volume or the optical density of platelets (David et al. *Coll Surface B: Biointerfaces.* 1996; 6:101-14; Hubbell et al. *Thromb Haemost.* 1991; 65:601-7.). It has been previously shown that the static light scattering curves of two morphologically different platelet populations are therefore nearly the same (Maurer-Spurej et al. *Lab Invest* 2001; 81(4):581-592.). Therefore, this type of measurement is not adequate for measuring platelet quality.

Spurej et al. (Spurej et al. Experientia 1992; 48:71-79) have used dynamic light scattering (DLS) to estimate electrophoretic mobility and diffusion coefficient and obtain information about the morphology of platelets under physiological conditions. However, no correlation with platelet quality was measured and electrophoretic light scattering is difficult to implement as a routine technique. Furthermore the experiments were conducted on purified platelet samples which are not representative of platelet concentrates.

Bayer developed the H*System hematology analyzer (Zelmanovic D, Hetherington E J. *Vet Clin Path.* 1998; 27(1):2-9.) and the new ADVIA 120 (Bayer Diagnostics) (Zelmanovic et al. United States patent, Oct. 6, 1998, U.S. Pat. No. 5,817,519.). Both instruments measure static light scattering to determine platelet activation. Several assumptions are made: 1. The shape of platelets is spherical. 2. Platelet density decreases with activation due to the release of granule content. 3. The refractive index of a platelet is extracted from a look-up table generated with latex spheres (Chapman et al. *Thromb Haemost.* 2003; 89(6):1004-15.). It is quite obvious that this approach is mathematically demanding and not very flexible.

Special light scattering instruments were developed that utilize static light scattering to measure microaggregation (David et al. *Coll Surface B: Biointerfaces.* 1996; 6:101-14; Eto et al. *Cardiovasc Res.* 1998; 40(1):223-9; Tomida et al. *Thromb Res* 1998;92:221-228; Yabasaki K, Kokufuta E. *Langmuir.* 2002; 18:39-45.) taking advantage of the fact that microaggregates scatter much more light than single platelets. The Japanese company Kowa brought several versions of this instrument to the market (PA-100, PA-200). However, these instruments are not designed to measure platelet morphology.

Furthermore, while some of the parameters discussed above have been linked to platelet activation there exist no solid evidence that they correlate with platelet quality in the sense of being suitable for blood transfusion.

Therefore, no test exists to rapidly and routinely measure platelet quality and platelet concentrates are released without quality testing. About 65,000 platelet concentrates have to be discarded by Canadian Blood Services because they reach their 5-day expiry date before they can be transfused. This translates to a loss of several million dollars. Similar discard rates are encountered in major blood banks around the world. With the implementation of bacterial testing and pathogen inactivation, platelet quality remains the major determinant for the out-date of platelet concentrates.

In view of the above it would be highly desirable to have a simple and rapid method for determining platelet quality.

SUMMARY OF THE INVENTION

There is therefore provided a method for determining platelet quality that is fast and reliable. The method uses dynamic light scattering (DLS) whereby certain parameters are derived from the DLS measurements and correlated with platelet quality. The method is rapid, requiring only a few steps and small sample quantities.

In one embodiment of the invention the DLS parameter is selected from the hydrodynamic radius, the relative number of platelet-derived microparticles in the solution and the relative number of platelet-derived microparticles in the solution in response to temperature variations.

The correlation between the quality of platelets and DLS parameters may also be derived from a combination of the parameters. Thus in one embodiment of the invention there is also provided a computational matrix in which the DLS parameters are combined to generate a combined value indicative of platelet quality. Such a combined value can increase the level of confidence in the determination of platelet quality of a sample.

BRIEF DESCRIPTION OF THE DRAWINGS

Further features and advantages of the present invention will become apparent from the following detailed description, taken in combination with the appended drawings, in which.

DETAILED DESCRIPTION OF THE PREFERRED EMBODIMENT

In the present specification by platelet quality, or quality of a sample comprising platelets, it is meant a measure indicative of the suitability of a platelet preparation for transfusion into an animal such as a human.

In one aspect of the present invention dynamic light scattering (DLS) is used to obtain parameters related to platelet characteristics that correlate with platelet quality. Dynamic light scattering (DLS) is also called quasi-elastic light scattering, photon-correlation spectroscopy or laser Doppler velocimetry (Logean et al. *Applied Optics.* 2000; 39: 2858-2862). The term dynamic indicates that particles size is not calculated from the scattering intensity but from intensity fluctuations caused by the Brownian motion of particles in solution (Mattley et al. *Photochem Photobiol.* 2000; 71(5):610-619; Ren et al. *Microvasc Res.* 1995; 49:233-245.). Instruments to measure DLS and algorithms to derive parameters from measurements are well known in the art (see for example Maurer-Spurej et al. *Lab. Invest.* 2001; 81(4):581-592 and references cited therein).

Figure 1:
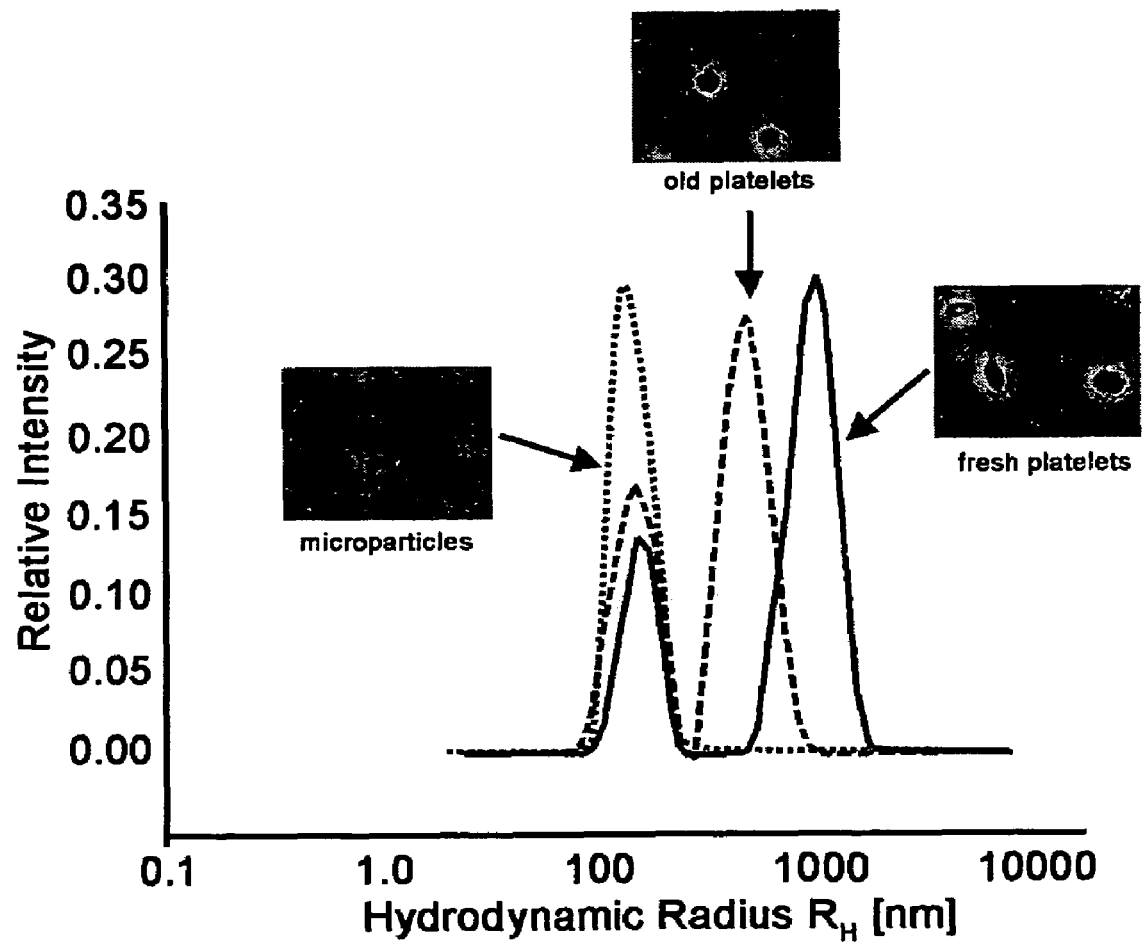
FIG. 1 is a graphic of the relative intensity of a dynamic light scattering signal as a function of the hydrodynamic radius ($R_H$) for fresh platelets (solid line), outdated platelets (dashed line) and after filtration of the sample to remove larger particles, phase contrast microscopy pictures of the three different samples are also shown.

DLS measurements of platelet concentrates were correlated with established assays to assess platelet quality in platelet concentrates. In one embodiment of the invention, the hydrodynamic ratio ($R_H$) of a platelet concentrate was measured. $R_H$ is based on Brownian motion of platelets in solution which causes fluctuations of the scattered light. Well known mathematical algorithms can be used to calculate the hydrodynamic radius ($R_H$) from these fluctuations. $R_H$ is an indicator of the average size and shape of platelets. FIG. 1 shows an $R_H$ distribution profile of fresh (solid line) and old (out-dated) (dashed line) platelets where old platelets exhibit a smaller $R_H$ than fresh platelets.

Figure 2:
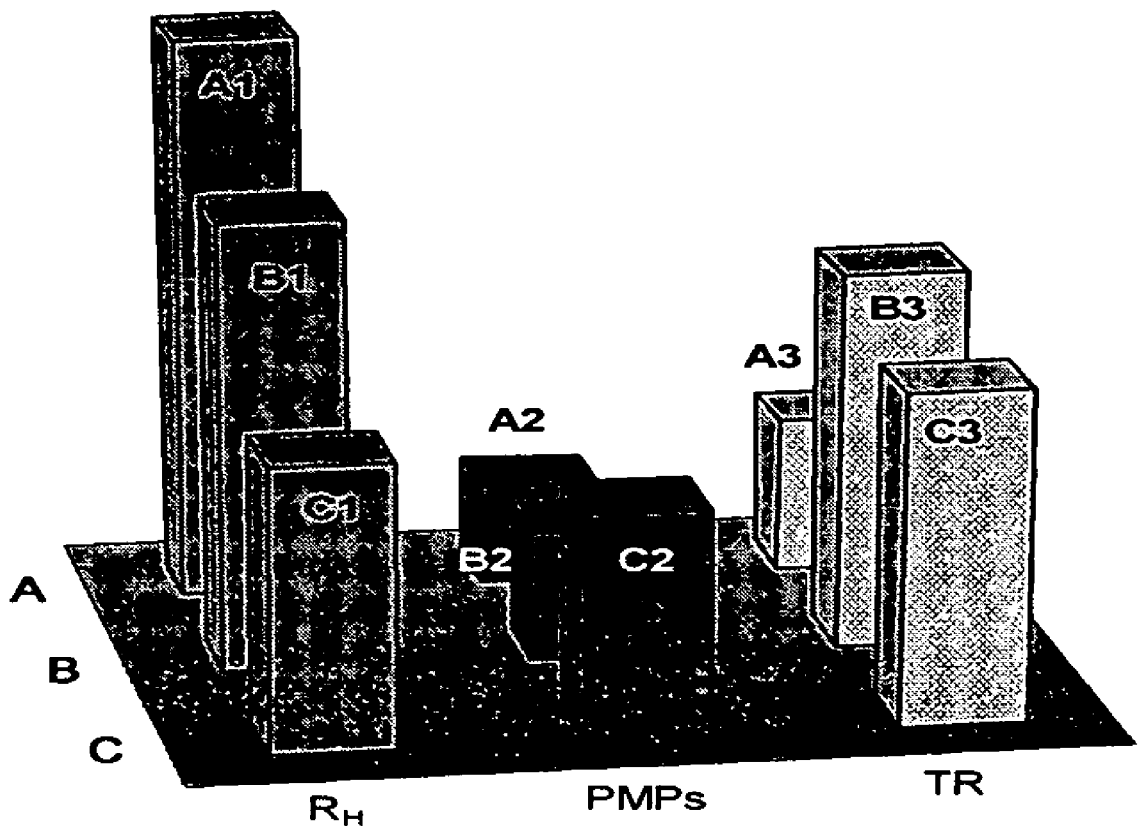
FIG. 2 is a bar graph representing measurements of $R_H$, relative number of platelet derived microparticles (PMP) and temperature response (TR) using DLS at three time points A,B and C corresponding to fresh platelets, 5 days old platelets and 6 days old platelets (1 day outdated) respectively.

In a time course assessment of $R_H$ (FIG. 2) it is shown that the $R_H$ of platelets diminishes significantly as they get older. At day five (B1) $R_H$ is approximately 75% of the original value for fresh platelet and by day six the $R_H$ reaches approximately 50% of its original value. Clearly, the $R_H$ of outdated platelets is reduced significantly. Thus the $R_H$ of a platelet concentrate can be measured and compared to an average $R_H$ value obtained, for example, from a statistically significant number of platelet concentrates for which the quality has been previously determined using at least one independent standard method such as the manual morphology scoring method to determine platelet quality. When the $R_H$ measured in a platelet concentrate is lower than the average $R_H$ value for fresh platelets by more than a predetermined cut-off percentage, the concentrate can be classified as being out-dated or unsuitable for transfusion.

Preferably the cut-off percentage is about 25% and most preferably about 50% of the average $R_H$ value. It will however be appreciated that the value of the cut-off percentage may vary depending on factors such as the health and the tolerable level of platelet activation of the recipient. It will also be appreciated that the average value of $R_H$ may have to be re-evaluated if the protocol for the preparation of the concentrate has changed.

In another aspect of the invention the relative number of platelet-derived microparticles was also found to correlate with platelet quality. Platelet-derived microparticles are much smaller than platelets and cause significantly faster scattering fluctuations leading to a smaller $R_H$ distribution. Platelet microparticles are membrane vesicles released by platelets during activation, and carry at least some antigens characteristic of intact platelets, chiefly GPIIb-IIIa and GPIb (Horstman L L, Ahn Y S. *Crit Rev Oncol/Hematol.* 1999; 30:111-142.). They are not detected by ordinary platelet counting methods and difficult to reproducibly measure by flow cytometry. It has been shown that the formation of microparticles is an indicator for platelet activation (Ando et al. *Kidney Int.* 2002; 62(5):1757-1763.). Indeed, in a preliminary study that focused on immobilizing microparticles for visualization on the microscope, the present inventor was able to detect fluorescently labeled antibodies to CD42 on microparticles.

It was found that fresh platelet concentrates contain bigger platelets and fewer microparticles (FIG. 1, solid line) relative to out-dated concentrate. Without wishing to be bound by theory, out-dated platelet concentrates are believed to contain smaller platelets because they bud off more microparticles (dashed line). After filtration of a platelet concentrate, only microparticles are left (dotted solid line).

Phase contrast microscopy images (FIG. 1) support the DLS results indicating the expected platelet morphology of fresh and old platelets and the absence of platelets in the sample of microparticles after filtration.

A time course study of the relative number of microparticles in a platelet concentrate shows (FIG. 2) that the number of microparticles remains low up to day five but increases significantly by day six at which time the platelets are out-dated as measured by standard methods.

That the parameters measured by DLS correlate with platelet quality was demonstrated by comparing the DLS results with results from tests using standard methods that are well known in the art to be indicative of platelet quality. Among these, morphology scoring is considered one of the most accurate and reliable test to determine platelet quality (viability). The results of morphology scoring (Kunicki morphology scoring) for the samples used in the DLS assay are summarized in table 1. It can be seen that the reduction in $R_H$ at day six corresponds to a reduction in morphology scoring indicative of out-dated platelets. Similarly, the increase in the relative number of microparticles at day six also correlates with the reduction in morphology scoring.

TABLE 1

Comparison of current methods with DLS parameters

| | DLS | | | Morphology | Flow Cytometry | | Extent of | Hypotonic |
| | diameter 2 × RH | micro-particles | pH | Score | CD62 | CD63 | Shape Change | Shock |
| Sample | Nm | % | — | (0-400) | % | % | % | % |
| fresh | 2150 ± 160 | 29 | 7.5 ± 0.1 | 330 ± 45 | 21 ± 9 | 6 ± 3 | 18 ± 2 | 28 ± 10 |
| out-dated | 1200 ± 230 | 41 | 7.1 ± 0.1 | 250 ± 30 | 29 ± 12 | 18 ± 6 | 10 ± 2 | 15 ± 7 |

Platelet activation was also used to correlate DLS results with platelet quality. Platelet activation is associated with conformational changes and expression of platelet integrins. The presence of CD62 and CD63 was measured using fluorescently labeled anti-CD62 and anti-CD63 monoclonal antibodies. The results (Table 1) clearly indicated an increase in these platelet activation markers in out-dated platelets. In this respect, the DLS results for $R_H$ and relative number of microparticles in out-dated platelets correlated with the increase in CD62 and CD63.

The pH of platelet concentrate solutions is also an indicator of ageing. During storage platelets metabolize nutrients aerobically to lactate and $CO_2$. Once all nutrient is used up or platelets lose their viability they switch to anaerobic metabolism and produce lactic acid which decreases the pH. Therefore, currently used plastic bags for platelet storage need to be gas permeable to balance the need for oxygen and the removal of carbon dioxide during aerobic metabolism and to maintain the pH during this phase. Table 1 indicates that lower pH values were obtained for out-dated platelet concentrates that correlated with the DLS results.

Hypotonic shock response and extent of shape change are yet other tests that can be performed to measure platelet ageing. The tests can be performed using a spontaneous platelet aggregation method. These two parameters can be measured in a spontaneous platelet aggregation (SPA) measuring device. For the hypotonic shock response water is added to platelet concentrate in a glass cuvette and the ability of platelets to remove the entering water back out (reverse swelling) is measured as a change in light transmission from the swollen to the recovered cells. Viable, fresh platelets are better able to respond to hypotonic shock than old platelets but the variability of the results is large. The results of the experiments (Table 1) indicate that these parameters also correlate with the DLS results.

Figure 3A:
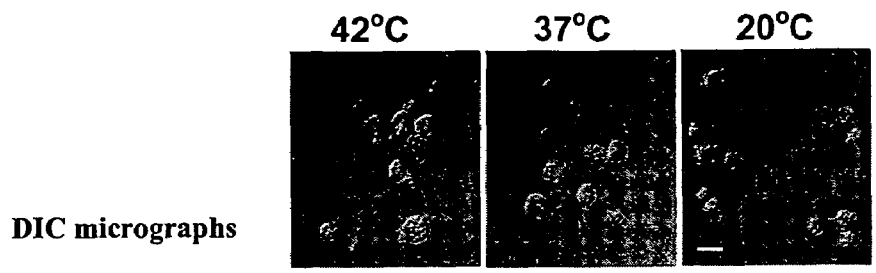
FIG. 3A shows differential interference contrast micrographs showing the morphology of platelets fixed in plasma at the indicated temperature.
Figure 3B:
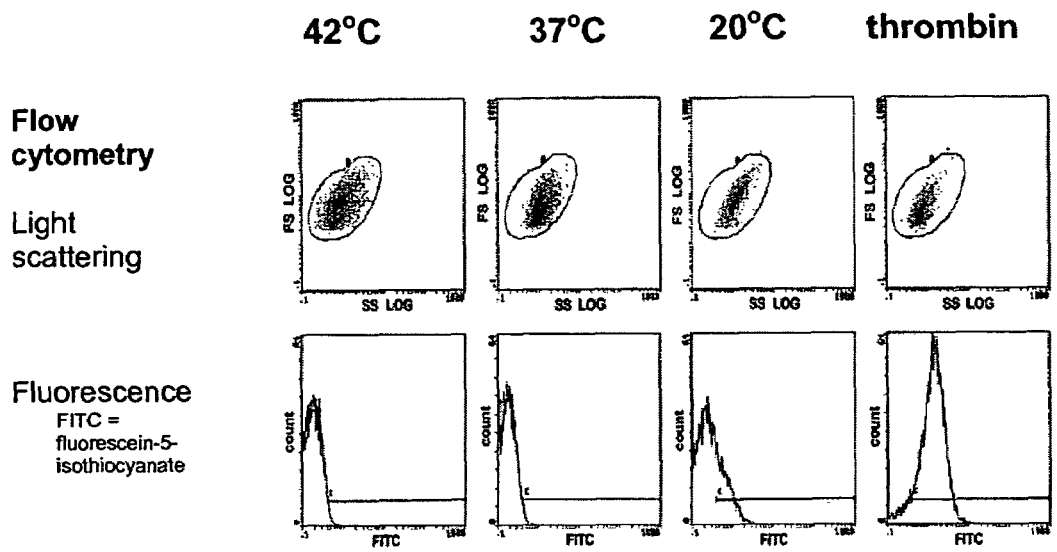
FIG. 3B shows flow cytometry scatter plots (log side scattering vs. log forward scattering) and fluorescence histograms (FITC fluorescence vs. platelet count) indicating binding of FITC-labeled PAC-1 antibodies to activated GPIIb-IIIa.
Figure 4:
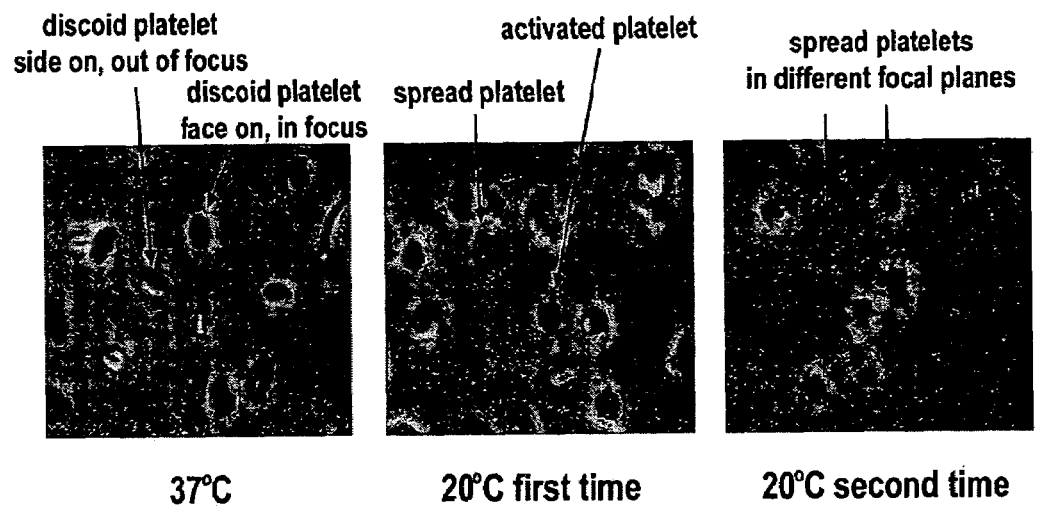
FIG. 4 shows phase contrast micrographs of fresh, resting platelets in citrate anticoagulated plasma at 37° C., activated after a first cooling at 20° C. and after rewarming and a second cooling at 20° C.

Fresh platelets activate at 4° C. (Hoffmeister et al. *Cell* 2003; 112:87-97.) but platelets are also sensitive to temperatures close to room temperature and change their morphology when exposed to 20° C. for 10 minutes (Maurer-Spurej E, and Devine D V. *Lab Invest.* 2001; 81(11):1517-26.) The temperature dependent platelet activation correlates with a significant increase in expression of activated GPIIb-IIIa ($\square_{IIb}\square_3$ integrin) as demonstrated by flow cytometry (FIGS. 3A and 3B), which is the binding site for fibrinogen and leads to crosslinking of platelets. While not wishing to be bound by theory, ongoing research suggests that the response of platelets to low temperature is a physiologic response involving serotonin and correlates with platelet viability. It was also reported that the morphological changes subsequent to low temperature exposure are reversible (Maurer-Spurej et al. *Lab Invest* 2001; 81(4):581-592.) which is in agreement with other reports (Michelson et al. *Thromb Haemost.* 1994; 71(5):633-640; Hartwig J H. Platelet structure. In: Platelets. (editor: A D Michelson). Academic Press 2002; 37-52.), in particular after transfusion (Rinder et al. *Transfusion.* 2003; 43(9):1230-7.). However, in experiments conducted by the present inventors it has been shown that the reversibility of temperature-dependent platelet activation is decreased when platelets have been previously activated (FIG. 4). Thus it can be seen in FIG. 4 that the first cooling to 20° C. causes shape changes and spreading of a few platelets. The second cooling to 20° C. (after re-warming) leads to microaggregates formation, spreading and cell fragmentation. These results correlate with DLS measurements showing that the relative number of microparticles in fresh platelets that have been temperature activated is lower than that of five or six days old platelets, which can be considered to have been activated. Therefore changes in the relative number of microparticles in platelets concentrates subsequent to temperature activation can also be used as an indicator of platelet quality.

The duration of incubation at a given temperature necessary to produce platelet activation may vary depending on the volume to be heated and the particular way in which the sample is heated. Once the temperature of the sample has reached the desired set point, platelet activation may be quite rapid and may occur, for example, in a few minutes.

Figure 5:
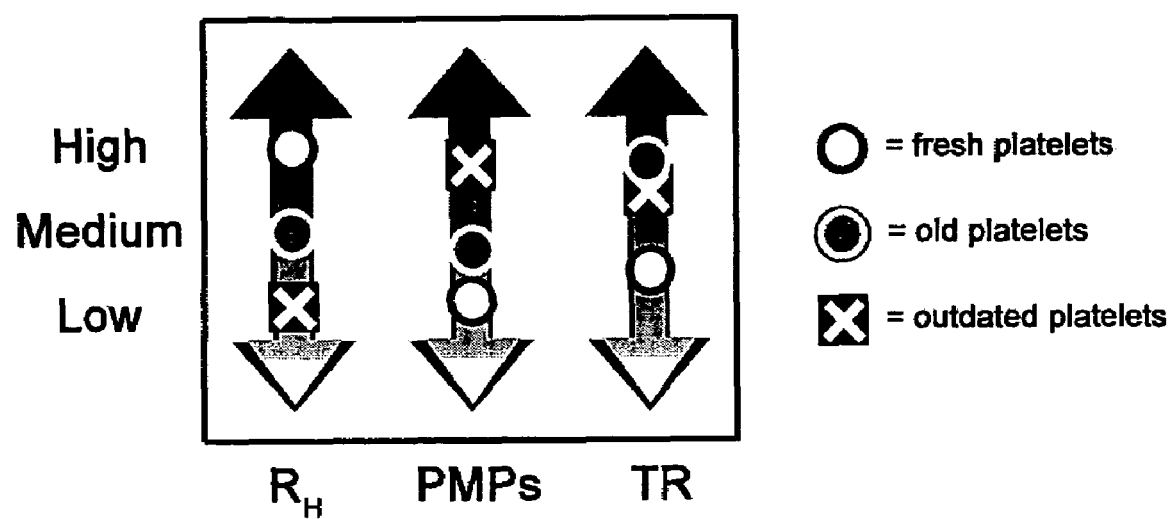
FIG. 5 is a schematic representation of an example of a computational matrix incorporating DLS parameters and used to assess platelet quality.

It will be appreciated that platelet characteristics derived by DLS measurements such as $R_H$ and relative number of microparticles (direct measurement or following temperature activation) can be used independently or in combination to assess platelet quality. The three independent parameters can define a computational matrix where each platelet concentrate sample is represented by a unique combination of results. A schematic representation of an example of a computational matrix is shown in FIG. 5 (corresponding to the results shown in FIG. 2). In sample A (fresh platelets) $R_H$ was high ($A1_{high}$), the number of microparticles was low ($A2_{low}$) and the response to temperature stress was not very pronounced ($A3_{medium}$). In contrast, for sample C (out-dated platelets) $R_H$ was low ($C1_{low}$), the number of microparticles was high ($C2_{high}$) and there was a pronounced response to temperature stress ($C3_{high}$).

Numerical values can be attributed to the DLS derived parameters that are indicative of platelet quality and these values can be combined to generate a combined value that can be used to determine platelet quality with a higher degree of confidence than for each parameter considered independently. Such a combination may also be a weighted combination in which each parameter is assigned a weighting factor.

EXAMPLE

In one experiment, fresh platelets have been determined to have an $R_H$ of 950±60 nm while out-dated platelets had an $R_H$ of 670±55 nm. Therefore in one embodiment of the method the platelets may be considered out-dated when the $R_H$ is lower than approximately 700 nm.

The embodiment(s) of the invention described above is (are) intended to be exemplary only. The scope of the invention is therefore intended to be limited solely by the scope of the appended claims.

I claim:

1. A method of determining the quality of a sample of platelets using dynamic light scattering, the method comprising:
   a. obtaining a sample of platelets (I);
   b. collecting dynamic light scatter from the sample of platelets;
   c. calculating an average hydrodynamic radius of the platelets in the sample based on the dynamic light scatter;
   d. measuring a temperature response of the platelets in the sample, said temperature response comprising:
      i. varying the temperature of the sample, by cooling the sample to cause platelet activation;
      ii. repeating the steps (b)-(c) above, wherein a temperature response is detected as a change in average hydrodynamic radius in the platelet sample resulting from varying the sample temperature;
   e. comparing the average hydrodynamic radius and the temperature response to the values obtained from a fresh platelet sample (II); and,
   f. concluding that the platelet sample (I) is out-dated wherein:
      i. the average hydrodynamic radius of the platelet sample (I) is less than 75% of the average hydrodynamic radius of a fresh platelet sample (II); and
      ii. the temperature response of the platelet sample (I) is less responsive relative to the temperature response of the fresh sample (II).

2. The method of claim 1 wherein the average hydrodynamic radius and the temperature response are each weighted by respective numerical weighting factors to compute a value which, when the value is compared to a value selected from a pre-determined range of acceptable values, is indicative of the quality of the sample.

3. The method of claim 1 wherein the sample of platelets (I) is taken from a concentrate.

4. The method of claim 1 wherein, in step (f)(i), the average hydrodynamic radius is less than 50% of the average hydrodynamic radius of a fresh platelet sample (II).

5. The method of claim 1 wherein the temperature response comprises activating the sample of platelets by incubating the cooled sample at a temperature between 20 and 37 degrees Celsius.

6. A method of determining the quality of a sample of platelets using dynamic light scattering, the method comprising:
   a. obtaining a sample of platelets (I);
   b. collecting dynamic light scatter from the sample of platelets;
   c. calculating the number of platelets in the sample;
   d. calculating the number of platelet-derived microparticles based on the dynamic light scatter in the sample; and,
   e. calculating the relative number of platelet-derived microparticles based on the dynamic light scatter, comprising calculating the number of platelet-derived microparticles relative to the number of platelets in the sample; and,
   f. measuring a temperature response of the platelets in the sample, said temperature response comprising:
      i. varying the temperature of the sample, by cooling the sample to cause platelet activation;
      ii. repeating the steps (b)-(e) above, wherein a temperature response is detected as a change in the relative number of platelet-derived microparticles in the platelet sample resulting from varying the sample temperature;

g. comparing the relative number of platelet-derived microparticles and the temperature response to the values obtained from a fresh platelet sample (II); and, h. concluding that the platelet sample (I) is out-dated wherein:
  i. the relative number of platelet-derived microparticles versus the number of platelets in the sample of platelets (I) is greater than 35%; and,
  ii. the temperature response of the platelet sample (I) is less responsive relative to the temperature response of the fresh sample (II).

7. The method of claim 6 wherein the relative number of platelet-derived microparticles and the temperature response are each weighted by respective numerical weighting factors to compute a value which, when the value is compared to a value selected from a pre-determined range of acceptable values, is indicative of the quality of the sample.

8. The method of claim 6 wherein the sample of platelets (I) is taken from a concentrate.

9. The method of claim 6 wherein the temperature response comprises activating the sample of platelets by incubating the sample at a temperature between 20 and 37 degrees Celsius.

10. A method of determining the quality of a sample of platelets using dynamic light scattering, the method comprising:
  a. obtaining a sample of platelets (I);
  b. collecting dynamic light scatter from the sample of platelets;
  c. calculating the number of platelets in the sample;
  d. calculating an average hydrodynamic radius of the platelets in the sample based on the dynamic light scatter;
  e. calculating the number of platelet-derived microparticles based on the dynamic light scatter in the sample; and,
  f. calculating the relative number of platelet-derived microparticles based on the dynamic light scatter, comprising calculating the number of platelet-derived microparticles relative to the number of platelets in the sample; and,
  g. measuring a temperature response of the platelets in the sample, said temperature response comprising:
    i. varying the temperature of the sample, by cooling the sample to cause platelet activation;
    ii. repeating steps (b)-(f) above, wherein a temperature response is detected as a change in average hydrodynamic radius and relative number of microparticles in the platelet sample resulting from varying the sample temperature;
  h. comparing the average hydrodynamic radius, the relative number of platelet-derived microparticles, and the temperature response to the values obtained from a fresh platelet sample (II); and,
  i. concluding that the platelet sample (I) is out-dated wherein:
    i. the average hydrodynamic radius of the platelet sample (I) is less than 75% of the average hydrodynamic radius of a fresh platelet sample (II); and,
    ii. the relative number of platelet-derived microparticles versus the number of platelets in the sample of platelets (I) is greater than 35%; and,
    iii. the temperature response of the platelet sample (I) is less responsive relative to the temperature response of the fresh sample (II).

11. The method of claim 10 wherein the step of determining the temperature response comprises steps of:
  a. cooling the sample to cause platelet activation which is detected as a change in average hydrodynamic radius; and
  b. cooling the sample a second time, after having re-warmed the sample, to cause subsequent platelet activation which is detected as a change in the relative number of platelet-derived microparticles.

12. The method of claim 10 wherein the average hydrodynamic radius, the relative number of platelet-derived microparticles and the temperature response of the platelet sample (I) are weighted by respective numerical weighting factors to compute a value which, when the value of the platelet sample is compared to the values obtained from a pre-determined range of acceptable samples, indicates the quality of the platelet sample (I).

13. The method of claim 10 wherein the sample of platelets (I) is obtained from a concentrate.

14. The method of claim 10 wherein, in step (i)(i), the average hydrodynamic radius is less than 50% of the average hydrodynamic radius of a fresh platelet sample (II).

15. The method of claim 10 wherein the temperature response comprises activating the sample of platelets by incubating the cooled sample at a temperature between 20 and 37 degrees Celsius.

* * * * *